US012558005B2

(12) United States Patent
Park

(10) Patent No.: US 12,558,005 B2
(45) Date of Patent: Feb. 24, 2026

(54) METHOD FOR NEAR FIELD COMMUNICATION CONNECTION OF CONTINUOUS BLOOD GLUCOSE MONITORING SYSTEM

(71) Applicant: I-SENS, INC., Seoul (KR)

(72) Inventor: Ji Sun Park, Seoul (KR)

(73) Assignee: I-SENS, INC., Seoul (KR)

( * ) Notice: Subject to any disclaimer, the term of this patent is extended or adjusted under 35 U.S.C. 154(b) by 1004 days.

(21) Appl. No.: 17/627,552

(22) PCT Filed: Mar. 13, 2020

(86) PCT No.: PCT/KR2020/003517
§ 371 (c)(1),
(2) Date: Jan. 14, 2022

(87) PCT Pub. No.: WO2021/010569
PCT Pub. Date: Jan. 21, 2021

(65) Prior Publication Data
US 2022/0257152 A1     Aug. 18, 2022

(30) Foreign Application Priority Data

Jul. 18, 2019     (KR) ........................ 10-2019-0087041

(51) Int. Cl.
*A61B 5/145*         (2006.01)
*A61B 5/00*          (2006.01)
*G06K 19/06*         (2006.01)
(52) U.S. Cl.
CPC .......... *A61B 5/14532* (2013.01); *A61B 5/002* (2013.01); *A61B 5/0024* (2013.01); *G06K 19/06037* (2013.01); *A61B 2505/07* (2013.01)
(58) Field of Classification Search
CPC ................ A61B 5/14532; A61B 5/002; A61B 5/0024; A61B 2505/07; G06K 19/06037
See application file for complete search history.

(56) References Cited

U.S. PATENT DOCUMENTS 9,730,268 B2     8/2017  Bolton et al.
9,787,941 B1 *  10/2017  Brooksby .............. H04N 7/147
(Continued)

FOREIGN PATENT DOCUMENTS

EP        1 424 817        6/2004
EP        3 261 357        12/2017
(Continued)

OTHER PUBLICATIONS

Examination Report No. 2 dated Mar. 17, 2023 for Australian Patent Application No. 2020313076.
International Search Report for PCT/KR2020/003517 mailed on Jun. 22, 2020 and its English translation from WIPO (now published as WO 2021/010569).
(Continued)

*Primary Examiner* — Alex M Valvis
*Assistant Examiner* — Jonathan M Haney
(74) *Attorney, Agent, or Firm* — WOMBLE BOND DICKINSON (US) LLP

(57) ABSTRACT

The present disclosure relates to a near field communication connection method of a continuous glucose monitoring system. A near field communication connection method of a continuous glucose monitoring system according to an embodiment of the present disclosure includes the steps of: acquiring connection information about a body attachable unit, which is attached to a human body and continuously monitors blood glucose, in order to connect communication between the body attachable unit and a communication terminal; using an identifier of the body attachable unit in the connection information to search for and select a body attachable unit matching the identifier of the body attachable unit from a device that can be communicatively connected to the communication terminal; and using an identification number of the body attachable unit in the connection information to connect the communication between the selected body attachable unit and the communication terminal.

7 Claims, 6 Drawing Sheets

(56) References Cited

U.S. PATENT DOCUMENTS

| | | | |
|---|---|---|---|
| 9,980,140 B1 | 5/2018 | Spencer et al. | |
| 2007/0237678 A1* | 10/2007 | Roesicke | A61B 5/0002 |
| | | | 422/82.01 |
| 2014/0051946 A1 | 2/2014 | Arne et al. | |
| 2014/0365694 A1 | 12/2014 | Bolton et al. | |
| 2015/0164323 A1 | 6/2015 | Holtzclaw | |
| 2015/0230085 A1 | 8/2015 | Xue | |
| 2017/0215029 A1 | 7/2017 | Makinouchi et al. | |
| 2018/0213583 A1 | 7/2018 | Al-Ali | |
| 2020/0375457 A1* | 12/2020 | Van Tassel | H04W 76/14 |
| 2021/0176810 A1 | 6/2021 | Chae | |

FOREIGN PATENT DOCUMENTS

| | | |
|---|---|---|
| JP | 2016-517317 | 6/2016 |
| JP | 2017-131319 | 8/2017 |
| JP | 2017-204014 | 11/2017 |
| JP | 2018-42058 | 3/2018 |
| KR | 10-2012-0045848 | 5/2012 |
| KR | 10-2015-0060109 | 6/2015 |
| KR | 10-2016-0007576 | 1/2016 |
| KR | 10-2016-0066532 | 6/2016 |
| KR | 10-2019-0049774 | 5/2019 |
| WO | 2008/154467 | 12/2008 |
| WO | 2019/112268 | 6/2019 |
| WO | 2021/010569 | 1/2021 |

OTHER PUBLICATIONS

Written Opinion of the International Searching Authority for PCT/KR2020/003517 mailed on Jun. 22, 2020 and its English translation by Google Translate (now published as WO 2021/010569).

European Search Report dated Apr. 18, 2023 for European Patent Application No. 20841157.9.

Office Action dated Jul. 9, 2024 for Japanese Patent Application No. 2023-211419 and its English translation from Global Dossier.

Office Action dated May 23, 2023 for Japanese Patent Application No. 2022-502305 and its English translation provided by Global Dossier.

International Preliminary Report on Patentability (Chapter I) for PCT/KR2020/003517 issued on Jan. 18, 2022 and its English translation from WIPO (now published as WO 2021/010569).

Examination Report No. 1 dated Nov. 7, 2022 for Australian Patent Application No. 2020313076.

Office Action dated Nov. 1, 2022 for Japanese Patent Application No. 2022-502305 and its English translation from Global Dossier.

Office Action dated Sep. 29, 2020 for Korean Patent Application No. 10-2019-0087041 and its English translation from Global Dossier.

Notice of Allowance dated May 27, 2021 for Korean Patent Application No. 10-2019-0087041 and its English translation from Global Dossier.

Office Action dated Dec. 3, 2024 for Japanese Patent Application No. 2023-211419 and its English translation by Google Translate.

KDDI Tobira: "What is Bluetooth? How is it different from Wi-Fi? A complete guide to connecting and using, it conveniently", May 15, 2014, pp. 1-3 (English translation provided by Applicant's foreign counsel).

* cited by examiner

[Fig. 1]
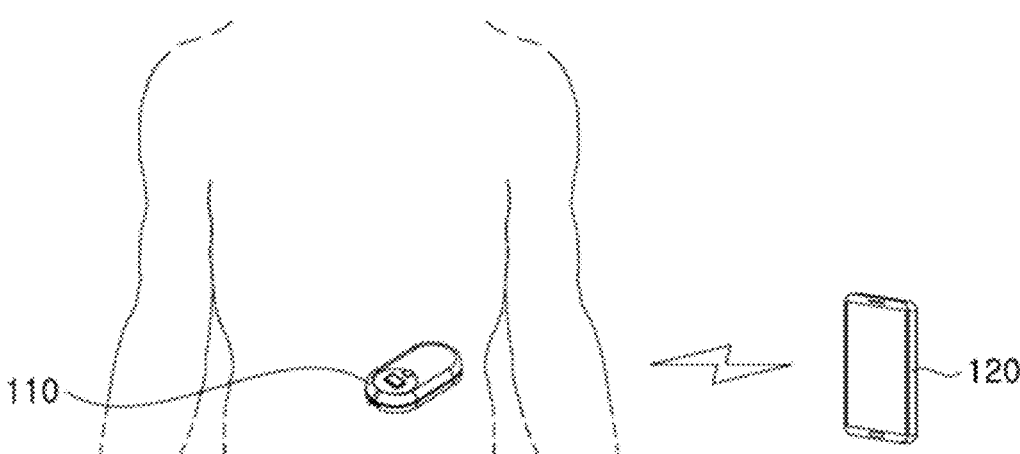
110        120
[Fig. 2]
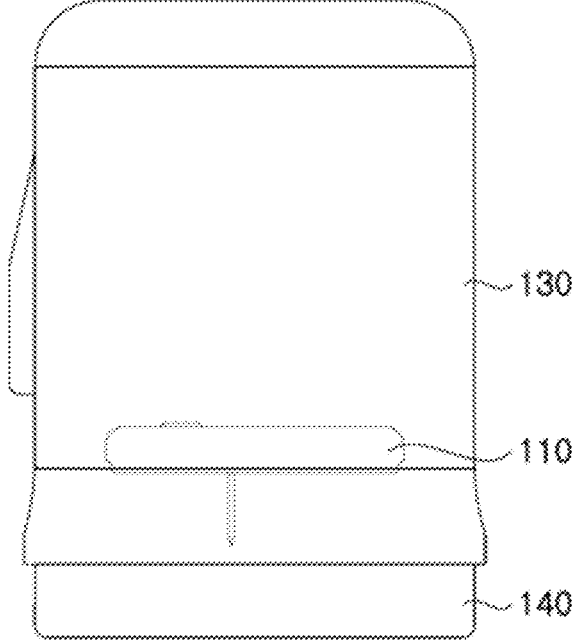
130
110
140

[Fig. 3]
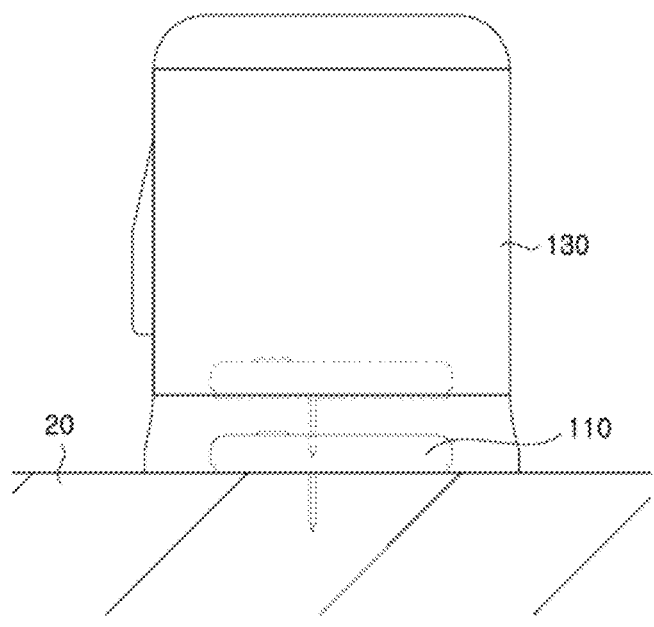
[Fig. 4]
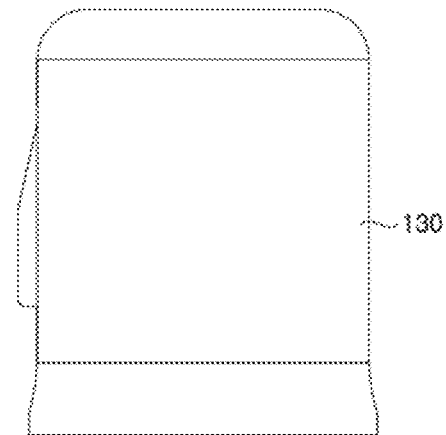
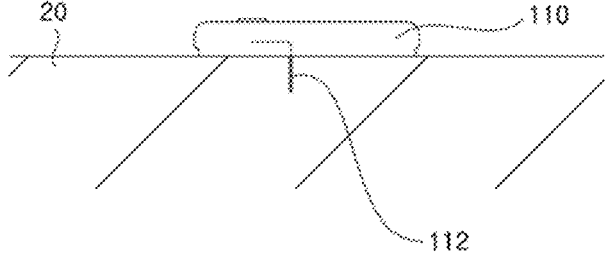

[Fig. 5]
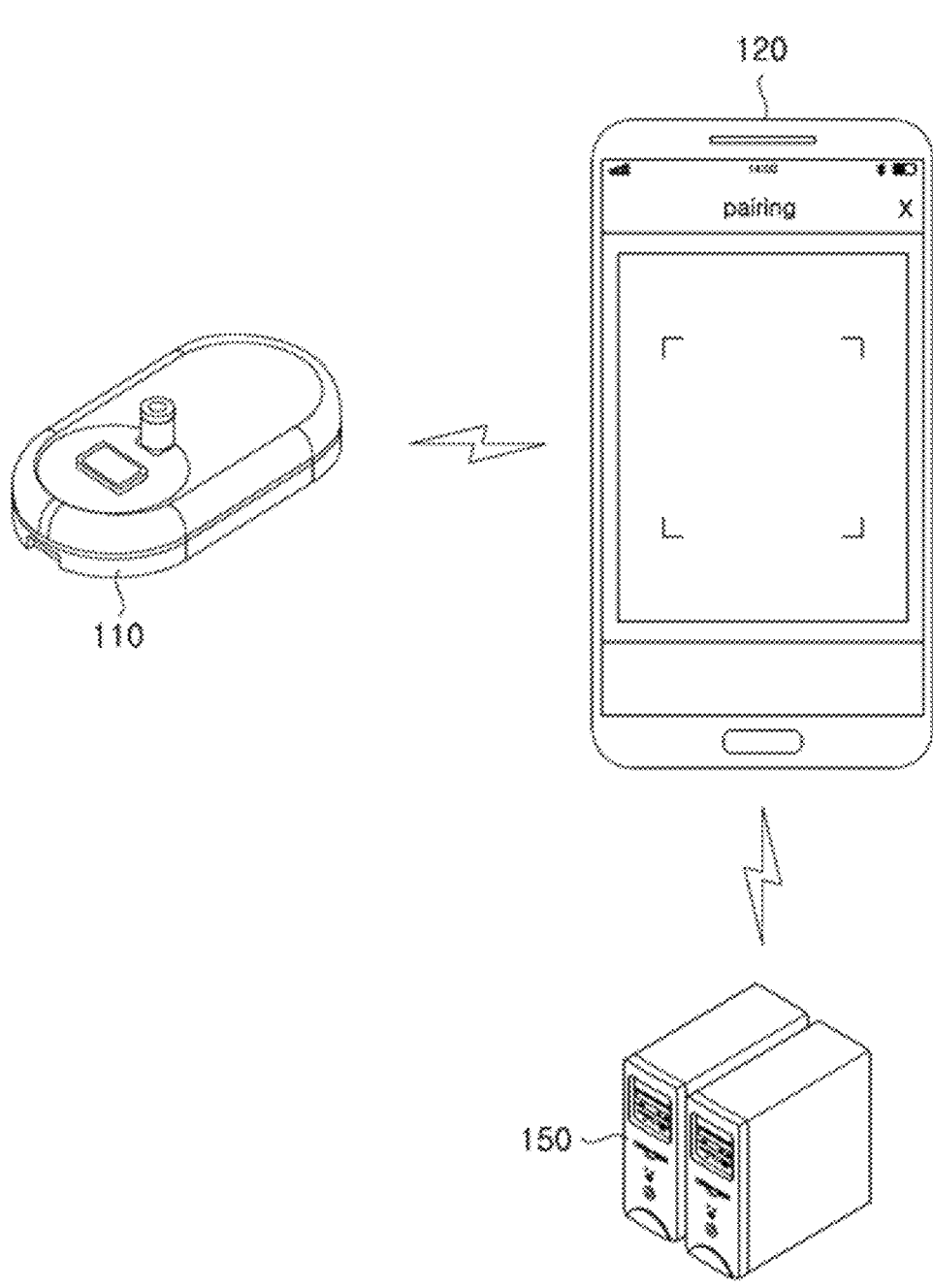

[Fig. 6]
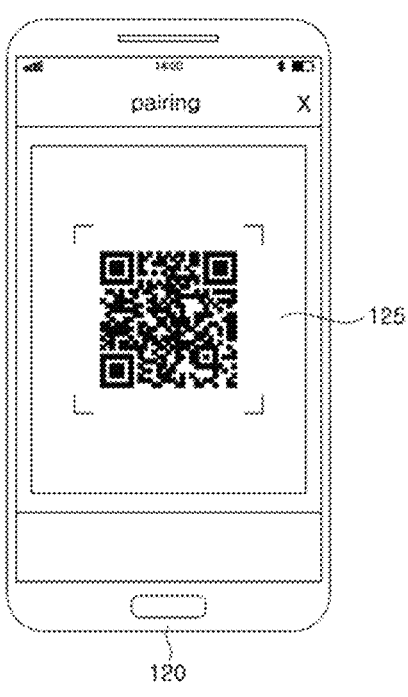
[Fig. 7]
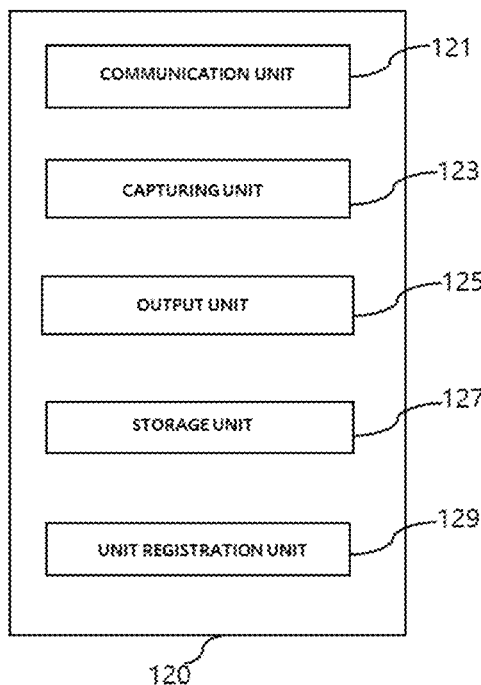

[Fig. 8]
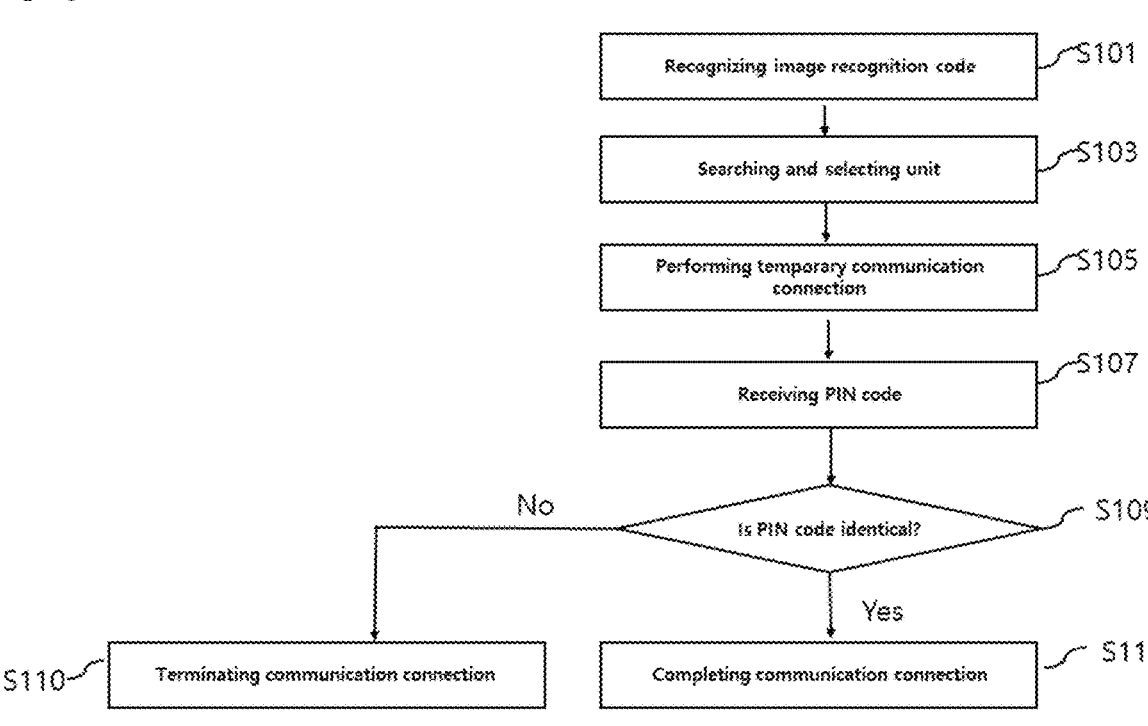

[Fig. 9]
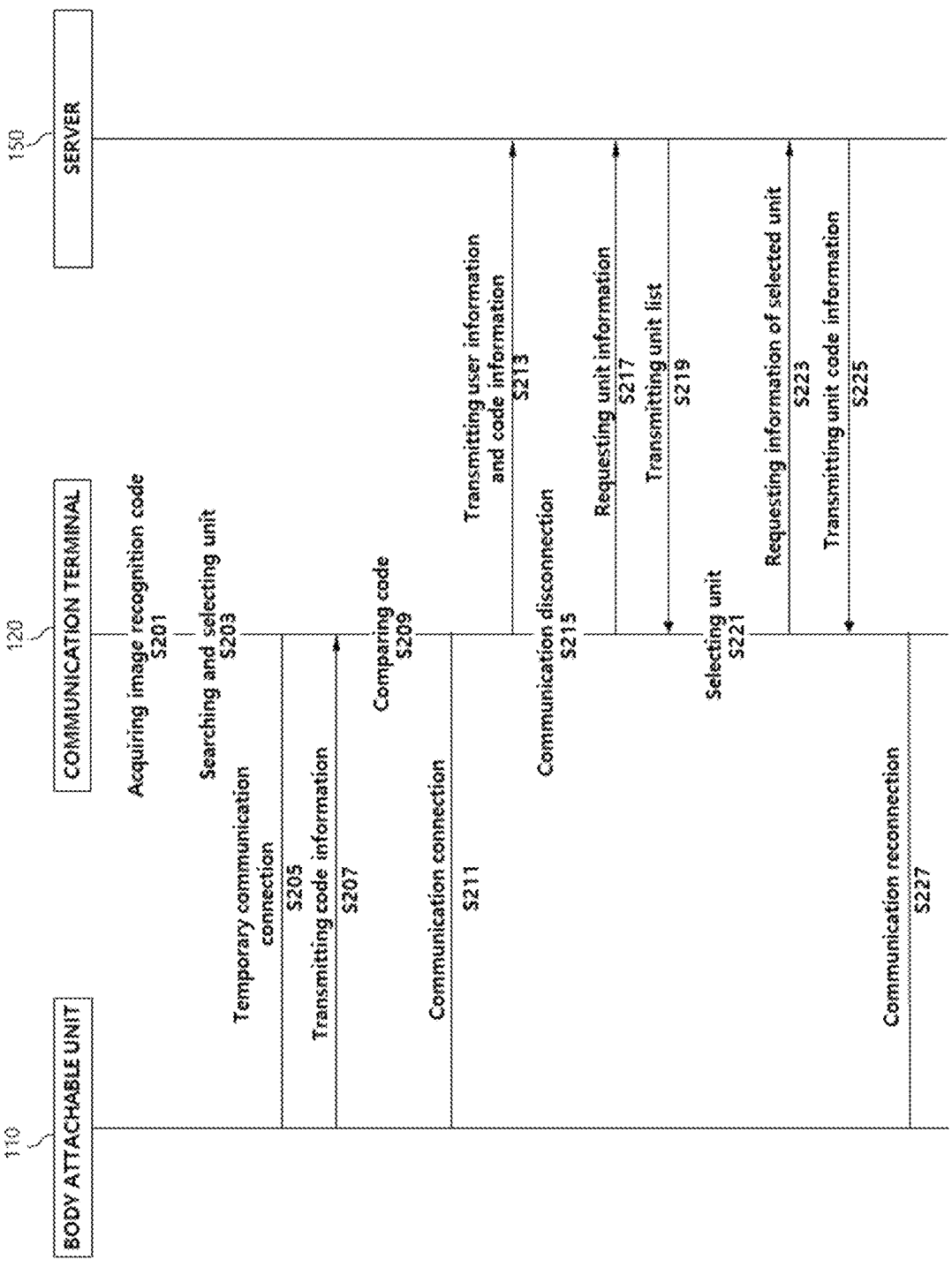

METHOD FOR NEAR FIELD COMMUNICATION CONNECTION OF CONTINUOUS BLOOD GLUCOSE MONITORING SYSTEM

CROSS-REFERENCE TO RELATED APPLICATIONS

The present application is the U.S. National Phase of PCT Application No. PCT/KR2020/003517 filed on Mar. 13, 2020, which claims the priority to Korean Patent Application No. 10-2019-0087041 filed on Jul. 18, 2019, the entire contents of which are incorporated herein by reference.

TECHNICAL FIELD

The present disclosure relates to a method for near field communication connection of a continuous blood glucose monitoring system, in more detail, a method for near field communication connection of a continuous blood glucose monitoring system which can quickly and precisely perform communication connection between a body attachable unit of the continuous blood glucose monitoring system for continuously measuring blood glucose and a communication terminal.

BACKGROUND

Diabetes is a major cause of death and a cause of disability worldwide, and therefore, many people have health problems due to diabetes. Specially, diabetes is a serious disease that causes heart and kidney disease, blindness, nerve damage and high blood pressure. According to a long-term clinical study, the incidence of complications can be significantly reduced by appropriately managing blood glucose levels. Therefore, it is important to continuously manage diabetes, an important factor is self-monitoring of blood glucose levels.

In response to this demand, a self-diagnosis biometer in which a user can check a blood glucose level of the user by himself or herself has been widely distributed and used. A conventional blood glucose meter measures the blood glucose level of the user by putting the user's blood on a sensor strip, which is a test strip. Accordingly, the sensor strip with the blood is inserted into the blood glucose meter, and the blood glucose level measured through the sensor strip is displayed on the blood glucose meter.

At this time, the blood glucose meter receives an electrical signal generated by an electrochemical reaction between the collected blood and the reactant in the sensor strip, and measures the blood glucose level. Such a finger prick method helps diabetic patients to manage blood glucose, but it is difficult to accurately identify the blood glucose levels which are being frequently changed because it shows only the result at the time of the measurement.

Diabetics patients generally experience hyperglycemia and hypoglycemia, an emergency may occur in the hypoglycemic conditions, and the patients may become unconscious or die if a hypoglycemic condition lasts for an extended period of time without the supply of sugar. Accordingly, although rapid discovery of the hypoglycemic condition is critically important for diabetics, blood-collecting type glucose monitoring devices intermittently measuring glucose have limited ability to accurately measure blood glucose levels.

To overcome such a drawback, continuous glucose monitoring systems (CGMSs) inserted into the human body to measure a blood glucose level every few minutes have been developed, and therefore easily perform the management of diabetics and responses to an emergency situation.

The continuous blood glucose measurement system comprises a body attachable unit for measuring blood glucose by being inserted to human body and collecting test substances such as blood of the user, and a communication terminal for communicating with the body attachable unit and displaying the blood glucose level measured by the body attachable unit. The process of the communication connection for transmitting and receiving data to and from each other is required.

In conventional art, a process of performing communication connection between the body attachable unit and the communication terminal using the Bluetooth communication standard is described as follows. If the Bluetooth is activated in the communication terminal, the communication terminal searches for devices connectable through the Bluetooth communication, and then displays identifiers of the devices connectable through the Bluetooth communication on a display unit of the communication terminal. The user selects an identifier corresponding to a body attachable unit which the user wishes to connect, and by inputting the unique number (for example, a PIN code) of the selected body attachable unit, connects the Bluetooth communication between the body attachable unit and the communication terminal.

As described above, many steps are required for connecting the communication between the body attachable unit and the communication terminal, and it is required to input a unique number of the body attachable unit consisting of complex numbers or characters. Generally, the body attachable units which are devices of measuring blood glucose information of users are used by older or younger aged people who are not accustomed to digital devices, the communication connection processes between the body attachable unit and the communication terminal described above is not easy for those people, and it is difficult of properly connecting the communication between the body attachable unit and the communication terminal by mistakenly inputting an unique number of the body attachable unit.

SUMMARY

Technical Problem

The present disclosure is invented to solve problems in conventional technique, and the purpose of the present disclosure is for providing a method for near field communication of a continuous blood glucose monitoring system in which communication connection between a body attachable unit and a communication terminal of the continuous blood glucose monitoring system can be more easily and intuitively performed.

Another purpose of the present disclosure is for providing a method for near field communication of a continuous blood glucose monitoring system in which, if the communication connection is disconnected after communication between a body attachable unit and a communication terminal is connected and information related to the body attachable unit is lost when trying to reconnect the communication connection, the communication connection between the body attachable unit and the communication terminal can be easily reconnected.

Solution to Problem

According to an embodiment of the present disclosure, a near field communication connection method may comprise: acquiring connection information of a body attachable unit, which is attachable to a human body to continuously monitor blood glucose, to connect communication between the body attachable unit and a communication terminal; using an identifier of the body attachable unit included in the connection information, searching for and select the body attachable unit corresponding to the identifier of the body attachable unit among one or more devices which are connectable to communicate with the communication terminal; and connecting communication between the selected body attachable unit and the communication terminal using an identification number of the body attachable unit included in the connection information.

The communication terminal may recognize an image recognition code including information of the identifier and the identification number to acquire the connection information of the body attachable unit.

The communication between the communication terminal and the body attachable unit may be connected according to a Bluetooth communication standard.

The image recognition code is a QR code or a bar code comprising one or more information.

The near field communication connection method may further comprise, when the body attachable unit is selected, receiving, by the communication terminal, the identification number of the selected body attachable unit from the selected body attachable unit, wherein the connecting of the communication between the selected body attachable unit and the communication terminal comprises, if the identification number of the selected body attachable unit received from the selected body attachable unit is identical to the identification number of the body attachable unit included in the connection information, connecting the communication between the selected body attachable unit and the communication terminal.

The near field communication connection method may further comprise, if the communication between the body attachable unit and the communication terminal is connected, transmitting information of a user of the communication terminal and the connection information of the body attachable unit to the server.

The information of the user may comprise one or more of an ID of the user logged in to the communication terminal, a serial number of the communication terminal, and a network address the communication terminal.

The near field communication connection method may further comprise: when the communication terminal and the body attachable unit are disconnected, requesting, by the communication terminal, information of the body attachable unit to the server to reconnect the communication between the communication terminal and the body attachable unit; transmitting, by the server, information including the identification number of the body attachable unit to the communication terminal; and reconnecting the communication between the communication terminal and the body attachable unit using the identification number of the body attachable unit received from the server.

The near field communication connection method may further comprise: when the information of the body attachable unit is requested to the server, transmitting, by the server, to the communication terminal a list of one or more body attachable units which have communicationally connected to the communication terminal; requesting, by the communication terminal, the information of the body attachable unit to which the communication terminal tries to be communicationally connected; and transmitting, by the server, the information including the identification number of the body attachable unit requested by the communication terminal, wherein the reconnecting of the communication between the communication terminal and the body attachable unit comprises reconnecting the communication between the communication terminal and the body attachable unit using the identification number of the body attachable unit received from the server.

The list of one or more body attachable units may be a list of one or more body attachable units of which use period does not expire.

Advantageous Effects of Invention

According to an embodiment of the present disclosure, by performing communication connection between a body attachable unit and a communication unit of a continuous blood glucose monitoring device using a Bluetooth communication standard, searching for an identifier of the body attachable unit using a connection code of the body attachable unit, and connecting the communication of the body attachable unit and the communication terminal using a identification information of the body attachable unit, the communication connection between the body attachable unit and the communication terminal can be intuitively and quickly performed.

Further, a communication terminal performs communication connection between a body attachable and the communication terminal by acquiring information related to the body attachable unit using an image recognition code, and therefore the communication between the body attachable unit and the communication terminal can be connected by only an user's action of capturing the image recognition code.

Additionally, because information of a body attachable unit acquired by a communication terminal is transmitted and stored to a server as back-up, the body attachable unit can be reconnected to the communication terminal using the back-up information stored to the server when the communication between the communication terminal and the body attachable unit is reconnected after that even though not having the information of the body attachable unit.

BRIEF DESCRIPTION OF THE DRAWINGS

FIG. 1 is a schematic diagram illustrating a continuous blood glucose monitoring system according to an embodiment of the present disclosure.

FIG. 2 is a figure illustrating an applicator for attaching a body attachable unit of a continuous blood glucose monitoring system to a human body according to an embodiment of the present disclosure.

FIGS. 3 and 4 are figures for illustrating a process of attaching a body attachable unit to a human body using an applicator in a continuous blood glucose monitoring system according to an embodiment of the present disclosure.

FIG. 5 is a figure for illustrating operations of communication connection between a body attachable unit and a communication terminal of a continuous blood glucose monitoring system according to an embodiment of the present disclosure.

FIG. 6 is a figure for illustrating a state that a communication terminal of a continuous blood glucose monitoring system recognizes a QR code for communication connection according to an embodiment of the present disclosure.

FIG. 7 is a block diagram for illustrating a communication terminal of a continuous blood glucose measuring system according to an embodiment of the present disclosure.

FIG. 8 is a flow chart for illustrating a near field communication connection method of a continuous blood glucose measuring system according to an embodiment of the present disclosure.

FIG. 9 is a flow chart for illustrating a near field communication connection method of a continuous blood glucose measuring system according to another embodiment of the present disclosure.

DETAILED DESCRIPTION OF EMBODIMENTS

Hereinafter, some preferred exemplary embodiments of the present disclosure will be described in detail with reference to the accompanying drawings.

FIG. 1 is a schematic diagram illustrating a continuous blood glucose monitoring system according to an embodiment of the present disclosure.

Referring to FIG. 1, a continuous blood glucose measuring system (100) according to an embodiment of the present disclosure comprises a body attachable unit (110) and a communication terminal (120).

The body attachable unit (110) can be attached to a human body, periodically extract the body fluid of the human body and monitor blood glucose. And, the measured blood glucose data is transmitted to the communication terminal (120). According to the present exemplary embodiment, communication between the body attachable unit (110) and the communication terminal (120) can be performed in an wireless communication type.

The body attachable unit (110) can be attached to a measurement position of the human body in order to periodically extract the body fluid of the human body and monitor the blood glucose, and a state that one end portion of an sensor included in the body attachable unit (110) is inserted to the human body can be maintained.

In the present embodiment, an applicator can be used for attaching the body attachable unit (110) to the human body. The applicator will be described in detail below.

The communication terminal (120) is implemented as a separate terminal outside the human body, and can receive signals from the body attachable unit (110) and store and display blood glucose data which is the measured result. In the present embodiment, a portable terminal (e.g. a smart phone, a tablet PC, or a notebook) configured to communicate with the body attachable unit (110) may be used as the communication termina (120). However, the communication terminal (120) is not limited thereto, and can be any type of a terminal which has a communication function and can install program or an application.

The communication terminal (120) stores information received from the body attachable unit (110) and can make and store it as database, and can output to display it using a display device so that a user can check it.

FIG. 2 is a figure illustrating an applicator for attaching a body attachable unit of a continuous blood glucose monitoring system to a human body according to an embodiment of the present disclosure, and FIGS. 3 and 4 are figures for illustrating a process of attaching a body attachable unit to a human body using an applicator in a continuous blood glucose monitoring system according to an embodiment of the present disclosure.

Firstly, an application (130) is now described by referring to FIG. 2. The body attachable unit (110) is mounted in the applicator (130), and the applicator (130) can be operated so that the body attachable unit (110) can be outwardly discharged to the outside of the applicator (130) by the manipulation of the user and then be attached to a specific portion of the human body of the user. In other words, the applicator (130) can be manufactured so that the body attachable unit (110) can be attached to skin of the human body by the operation of outwardly discharging the body attachable unit (110) mounted to the inside of the body attachable unit (110). Accordingly, the user can attach the body attachable unit (110) to his or her skin without separate additional manipulation.

As illustrated in FIGS. 2 to 4, the applicator (130) is formed to have a shape that one side of the applicator (130) is open, and the body attachable unit (110) is installed to the applicator (130) through the open side of the applicator (130). And, the body attachable unit (110) installed inside of the applicator (130) can be outwardly discharged by a one single time manipulation of the applicator (130), and the applicator (130) can be configured so that any other body attachable unit (110) cannot be inserted into the applicator (130) after one body attachable unit (110) is discharged. According to an embodiment of the present disclosure, the applicator (130) can be configured to be used as one single time only and be prevented from being reused. However, the present disclosure is not limited thereto, and the applicator (130) can be configured as being reusable if necessary.

Additionally, a separate and/or additional protection cap (140) can be separably coupled to the applicator (130) in order to block external exposure of the body attachable unit (110) in a state that the body attachable unit (110) is inserted in the inside of the applicator (130). After removing the protection cap (140) from the applicator (130), the user can manipulate the applicator (130) and outwardly discharge the body attachable unit (110) and attach the body attachable unit (110) to the human body.

A process of attaching the body attachable unit (110) to human body will be described in detail with reference to FIGS. 3 and 4.

Referring to FIG. 3, in a state that the protection cap (140) is separated or removed, an open side of the applicator (130) is closely placed on a specific part of skin (20) of the human body. In a state that the applicator (130) is closely placed on the skin (20) of the human body, the body attachable unit (110) is outwardly discharged from the applicator (130) and then attached to the skin (20).

And, as illustrated in FIG. 4, when the applicator (130) is moved away from the skin (20) of the human body, only the body attachable unit (110) maintains a state of being attached to the skin (20) of the human body. In this state, a sensor (112) is arranged to protrude from the body attachable unit (110) at the lower portion of the body attachable unit (110), and a part of the sensor (112) is inserted into the skin (20) by a needle installed at the applicator (130).

In the embodiment of the present disclosure, an adhesive tape is provided at a surface of the body attachable unit (20) contacting the human body so that the body attachable unit (110) can be attached to the skin (20), and a release paper can be attached to the surface of the adhesive tape contacting the human body to protect the adhesive tape. And, the release paper of the adhesive tape may be configured to be separated and removed from the adhesive tape during the operation of removing the protection cap (140) from the applicator (130).

For example, one side of the release paper is adhered to the protection cap (140), and therefore, when the user removes the protection cap (140) from the applicator (130), the release paper may be separated and removed from the adhesive tape together with the protection cap (140).

Additionally, a switching means can be installed to the body attachable unit (110), and the switching means is installed to operate the body attachable unit (110). The user can initiate to operate the body attachable unit (110) by using the switching means. Accordingly, if the body attachable unit (110) starts to operate, the body attachable unit (110) monitors the blood glucose of the human body using the sensor (112) and transmits blood glucose data which is the measured result to the communication terminal (120). In the present embodiment, the switching means can be implemented in various ways. Accordingly, if the switching means installed to the body attachable unit (110) is operated, the sensor (112) of which one end portion is inserted to the skin (20) and a circuit board (not shown) can be electrically connected to each other. Therefore, the sensor (112) is electrically connected with the circuit board and can measure the blood glucose of the human body.

FIG. 5 is a figure for illustrating operations of communication connection between a body attachable unit and a communication terminal of a continuous blood glucose monitoring system according to an embodiment of the present disclosure, and FIG. 6 is a figure for illustrating a state that a communication terminal of a continuous blood glucose monitoring system recognizes a QR code for communication connection according to an embodiment of the present disclosure.

Referring to FIGS. 5 and 6, a communication connection system (100) of a continuous blood glucose monitoring system is a system for communication connection of the body attachable unit (110) and the communication terminal (120), and comprises the body attachable unit (110), the communication terminal (120) and a sever (150). The present embodiment will be described with reference to FIGS. 1 to 4.

In the present embodiment, the communication between the body attachable unit (110) and the communication terminal (120) is implemented as near field communication, and as an example, the communication is performed according to a Bluetooth communication standard.

The body attachable unit (110) is attached to the human body in order to extract the body fluid of the human body and periodically measure blood glucose, and transmits the measured blood glucose data to the communication terminal (120). For this, the body attachable unit (110) comprises a sensor module and a sensor transmitter. The body attachable unit (110) can be attached to the human body by the applicator (130) described above, and in a state that the body attachable unit (110) is attached to the human body, the body attachable unit (110) monitors the blood glucose of the human body for a time period of approximately one (1) week to thirty (30) days. In this embodiment, the usable period of the body attachable unit (110) is identical to the usable period of the sensor module, and the usable period of the sensor module can be limited to a certain time period, such as about one (1) week, fifteen (15) days or thirty (30) days. When the usable period of the sensor module is expired, the blood glucose measurement is not performed any more even though the body attachable unit (110) is attached to the human body. Accordingly, if the usable period of the sensor module is expired, new body attachable unit (110) should be attached to the human body. In the present embodiment, the body attachable unit (110) and the applicator (130) can be configured to be one time disposable.

The communication terminal (120) receives the blood glucose data from the body attachable unit (110) through the communication connection with the body attachable unit (110), and displays the received blood glucose data so that the user can check the received blood glucose data.

The communication between the body attachable unit (110) and the communication terminal (120) can be performed through the Bluetooth communication, and the blood glucose data measured by the body attachable unit (110) can be transmitted to the communication terminal (120) through the Bluetooth communication. At this time, the body attachable unit (110) and the communication terminal (120) can perform a pairing process in which initial communication connection is performed. For this, the communication terminal (120) activates the Bluetooth communication, and searches for a device for pairing and is connected to the body attachable unit (110) and completes the pairing process.

During that time, the communication terminal (120) can acquire connection information on the body attachable unit (110) for the communication connection of the body attachable unit (110) and the communication terminal (120). In the present embodiment, the connection information on the body attachable unit (110) includes an identifier and/or a pin code of the body attachable unit (110). Here, the identifier and/or the pin code of the body attachable unit (110) can be provided using an image recognition code such as a QR code or bar code.

The image recognition code can be printed directly on the body attachable unit (110), and if necessary, can be printed at a package wrapping the body attachable unit (110). Alternatively, the image recognition code can be printed at the applicator (130) or the protection cap (140) described above if necessary.

Accordingly, if the user captures the image recognition code including the connection information of the body attachable unit (110) using the communication terminal (120), the communication of the body attachable unit (110) and the communication terminal (120) can be connected.

Therefore, as described above, when the communication of the body attachable unit (110) and the communication terminal (120) is connected, the blood glucose data can be transferred from the body attachable unit (110) to the communication terminal (120), and the communication terminal (120) receives and stores the blood glucose data and the blood glucose data can be displayed on the communication terminal (120).

In the present disclosure, the connection information included in the image recognition code may be an identifier and pin code information of the body attachable unit (110), the communication terminal (120) searches for the body attachable unit (110) using the identifier information of the body attachable unit (110) included in the image recognition code, and uses the pin code information of the body attachable unit (110) comprised in the image recognition code for the input of the pin code of the searched body attachable unit (110).

Accordingly, when the communication connection with the body attachable unit (110) and program or application for receiving, storing and outputting the blood glucose data are executed at the communication terminal (120), an authorization process for a user can be performed through a process such as a login. And, when the body attachable unit (110) is not communicationally connected to the communication terminal (120), a process for the communication connection with the body attachable unit (110) can be performed. During this process, the communication terminal (120) may output a display or interface for capturing an image recognition code of the body attachable unit (110).

Therefore, if the user captures the image recognition code of the body attachable unit (110) using the communication terminal (120), the communication terminal (120) can extract the connection information of the body attachable unit (110) included in the image recognition code. And, the communication terminal (120) searches for and selects a body attachable unit (110) corresponding to the identifier information of the body attachable unit (110) among devices, which can be communicationally connected with the communication terminal (120), using the identifier information of the body attachable unit (110) included in the connection information of the recognized body attachable unit (110).

Here, when the communication terminal (120) searches for a device for communication connection, a list of devices located within a communication range of the communication terminal (120) may be displayed on the communication terminal (120). At that time, the list can be displayed on the display unit (125) included in the communication terminal (120), although it is not limited thereto, and even though the list of the devices is searched by the communication terminal (120), it may not be outputted on the display unit (125).

When the identifier of the body attachable unit (110) included in the image recognition code is searched among the devices communicationally connectable to the communication terminal (120), the communication terminal (120) selects the body attachable unit (110) corresponding to the searched identifier. In this embodiment, the selection with respect to the body attachable unit (110) corresponding to the searched identifier can automatically performed by the communication terminal (120).

Likewise, when the body attachable unit (110) is selected by the communication terminal (120), the temporary communication connection between the communication terminal (120) and the body attachable unit (110) is performed. And, a PIN code which is a unique or identification number of the body attachable unit (110) is recognized by the communication terminal (120), and the PIN code information of the body attachable unit (110) included in the image recognition code image-inputted to the communication terminal (120) is recognizable.

The PIN code information of the body attachable unit (110) included in the image recognition code, when the PIN code information recognized by the communication terminal (120) and the PIN code information received by the body attachable unit (110) match each other, can complete the communication connection of the communication terminal (120) and the body attachable unit (110). At this time, the communication terminal (120) can receive the PIN code information included in the body attachable unit (110) from the body attachable unit (110) through the temporary communication connection of the communication terminal (120) and the body attachable unit (110).

The PIN code may be a code for two-way (or one-way) communication of the body attachable unit (110) and the communication terminal (120), and can perform a password code function for security of the Bluetooth communication. Such a PIN code may have the form of repeating the same number such as '0000', but not limited thereto, and if the security is necessary, four digits or six digits which are greater than four digits can be used, or the PIN code may have the form of combination of characters and numbers if necessary.

Likewise, the user can complete the communication connection of the body attachable unit (110) and the communication terminal (120) by only the action of capturing the image recognition code of the body attachable unit (110) using the communication terminal (120). Accordingly, the user does not need to search the body attachable unit (110) for the communication connection at the communication terminal (120), and does not have to input the PIN code for communication connection. Therefore, the user does not experience errors such as mistakenly searching the body attachable unit (110) or erroneously enter the PIN code.

The server (150) can receive information related to the body attachable unit (110) from the communication terminal (120) through the communication with the communication terminal (120). In this embodiment, the information related to the body attachable unit (110) may be information, for example, but not limited to, the identifier information of the body attachable unit (110) and the PIN code for communication connection of the body attachable unit.

And, the server (150) stores the information received from the communication terminal (120), and generates database with the stored information. Accordingly, when the authentication process with respect to the user is performed at the communication terminal (120) through a process of login and so on, the server (150) receives the user information from the communication terminal (120), and stores the received user information and the information regarding the body attachable unit (110) associated with each other.

FIG. 7 is a block diagram for illustrating a communication terminal of a continuous blood glucose measuring system according to an embodiment of the present disclosure.

Referring to FIG. 7, as described above, for the communication connection of the body attachable unit (110) and the communication terminal (120), the communication terminal (120) comprises a communication unit (121), a capturing unit (123), an output unit (125), a storage unit (127), and a unit registration unit (129).

The communication unit (121) is comprised for near field communication with the body attachable unit (110). In the present exemplary embodiment, the communication unit (121) communicates with the body attachable unit (110) according to the Bluetooth communication standard. However, the present disclosure is not limited thereto, and any other type of near field communication can be used if necessary.

The communication unit (121) can perform a pairing process for the communication connection with the body attachable unit (110), and the pairing process can be completed after a temporary communication connection process.

Additionally, after the communication unit (121) is communicationally connected with the body attachable unit (110) at least one time, the communication with body attachable unit (110) can be automatically performed if the body attachable unit (110) is located within a certain distance or the power of the body attachable unit (110) is operated.

The capturing unit (123) is included in the communication terminal (120), and is comprised for capturing an image recognition code of the body attachable unit (110). The capturing unit (123) may be a camera mounted to the communication terminal (120), and is configured to capture the image recognition code such as a QR code, a barcode and the like. The image captured by the capturing unit (123) can be outputted or displayed on the output unit (125), and if necessary, the captured image may be stored at the storage unit (127).

The output unit (125) is comprised in the communication terminal (120), and is included for outputting or displaying the image captured by the capturing unit (123). Accordingly, if the image recognition code is captured by the capturing unit (123), the output unit (125) displays the captured image. Additionally, as shown in FIGS. 5 and 6, a virtual guideline for guiding a position of an image recognition code can be displayed or provided on the output unit (125) so that the user can precisely capture the image recognition code with communication terminal (120).

Therefore, the user can change the position of the communication terminal (120) so that the image recognition code is located at or within the guideline indicated on the output unit (125) for capturing the image recognition code including identifier information and PIN code information of the body attachable unit (110).

The storage unit (127) can store image or video of image recognition codes captured by the capturing unit (123). In addition, identifier information and PIN code information of the body attachable unit (110) inputted through an image recognition code can be stored at the storage unit (127). As the identifier information and the PIN code information are stored at the storage unit (127), the communication terminal (120) can use the identifier information and the PIN code information stored at the storage unit when the communication terminal (120) is reconnected with the body attachable unit (110) after their communication connection is disconnected.

The unit registration unit (129) recognizes identifier information and PIN code information of the body attachable unit (110) from an image recognition code captured by the capturing unit (123). Therefore, the capturing unit (123) successfully captures an image recognition code, and the unit registration unit (129) recognizes identifier information and PIN code information of the body attachable unit (110) from the image recognition code captured by the capturing unit (123).

When the identifier information and PIN code information of the body attachable unit (110) is successfully recognized, the unit registration unit (129) searches for the body attachable unit (110), selects a body attachable unit corresponding to the identifier information, and completes the communication connection with the body attachable unit (110) using the recognized PIN code information.

Further, the unit registration unit (129) communicates with the server (150), and control the communication unit (121) such that the communication unit (121) transmits the identifier information and the PIN code information of the body attachable unit (110) recognized from the image recognition code to the server (150). Additionally, the communication unit (121) transmits information on a user, who is logged in to the communication terminal (120), to the server (150). By transmitting the user information and the identifier information and the PIN code information of the body attachable unit (110) recognized from the image recognition code to the server (150), the communication terminal (120) can receive and use the information transmitted to the server (150) when the communication terminal (120) is reconnected with the body attachable unit (110) for the communication connection with the body attachable unit (110).

FIG. 8 is a flow chart for illustrating a near field communication connection method of a continuous blood glucose measuring system according to an embodiment of the present disclosure.

The near field communication connection method of the continuous blood glucose measuring system according to an embodiment of the present disclosure is described by referring to FIG. 8. Further, with reference to FIGS. 1 to 7, the near field communication connection method of the continuous blood glucose measuring system according to an embodiment of the present disclosure is described herein.

Program or application installed to the communication terminal (120) for the communication connection of the body attachable unit (110) and communication terminal (120) is executed in the communication terminal (120), and a login process of a user can be performed if necessary. And, the communication terminal (120) recognizes an image recognition code for the communication connection with the body attachable unit (110), thereby acquiring connection information for the communication connection of the body attachable unit (110) (S101). In this step, the connection information included in the image recognition code may be identifier information and PIN code information of the body attachable unit (110).

The image recognition code may be directly printed on the body attachable unit (110), and if necessary, may be printed on a package wrapping the body attachable unit (110). Alternatively, it can be printed on the applicator (130) or the protection cap (140) described above if necessary.

Accordingly, the user can get the communication information of the body attachable unit (110) included in the image recognition code by capturing the printed image recognition code using the communication terminal (120).

As described above, if the communication terminal (120) receives the connection information of the body attachable unit (110), the communication terminal (120) searches for one or more devices located with a communicable range, and further search for one or more devices communicationally connectable with the communication terminal (120) among them. And, the communication terminal (120) searches for the body attachable unit (110) corresponding to the identifier information among the searched devices using the identifier information included in the connection information of the body attachable unit (110) through the image recognition code, and the communication terminal (120) selects the searched body attachable unit (110) (S103).

In this step, the communication terminal (120) selects a device corresponding to the identifier information recognized through the image recognition code among the searched devices, and the device corresponding to the identifier information is the body attachable unit (110). In this operation, the communication terminal (120) searches for the body attachable unit (110), and the output unit (125) outputs or displays an ongoing searching process, but it is not limited thereto, and the output unit (125) may output or display the searched result which is information of the selected body attachable unit (110) only.

If the communication terminal (120) selects the body attachable unit (110), the communication terminal (120) is temporarily communicationally connected to the body attachable unit (110). Accordingly, the communication terminal (120) can receive necessary information from the body attachable unit (110) temporarily communicationally connected.

Therefore, the communication terminal (120) receives information of the body attachable unit (110) comprising PIN code information from the body attachable unit (110) (S107). In this step, the information received by the communication terminal (120) from the body attachable unit (110) may comprise at least one of identifier information, a serial number and PIN code information of the body attachable unit (110).

And, the communication terminal (120) recognizes the PIN code information received from the body attachable unit (110) and the image recognition code and compares whether the PIN code information received from the body attachable unit (110) and the PIN code included in the image recognition code are identical to each other (S109).

Here, if the PIN code information received from the body attachable unit (110) and the PIN code included in the image recognition code match each other, the communication terminal (120) completes the communication connection with the selected body attachable unit (110) (S111).

However, if the PIN code information received from the body attachable unit (110) and the PIN code included in the image recognition code are different from each other, the communication terminal (120) does not proceed the communication connection with the selected body attachable unit (110) any more and terminates the communication (S110).

FIG. 9 is a flow chart for illustrating a near field communication connection method of a continuous blood glucose measuring system according to another embodiment of the present disclosure.

The near field communication connection method of the continuous blood glucose measuring system according to another embodiment of the present disclosure is described by referring to FIG. 9. Further, the present embodiment is described with reference to FIGS. 1 to 7, but the overlapped description with those embodiments may be omitted.

Program or application installed to the communication terminal (120) for the communication connection of the body attachable unit (110) and communication terminal (120) is executed in the communication terminal (120), and a login process of a user can be performed if necessary. And, the communication terminal (120) recognizes an image recognition code for the communication connection with the body attachable unit (110), thereby acquiring connection information for the communication connection of the body attachable unit (110) (S201). In this step, the connection information included in the image recognition code may be identifier information and PIN code information of the body attachable unit (110).

If the communication terminal (120) receives the connection information of the body attachable unit (110), the communication terminal (120) searches for one or more devices communicationally connectable with the communication terminal (120) among devices located with a communicable range. And, the communication terminal (120) searches for the body attachable unit (110) corresponding to the identifier information among the searched devices using the identifier information included in the connection information of the body attachable unit (110) through the image recognition code, and the communication terminal (120) selects the searched body attachable unit (110) (S203).

When the communication terminal (120) selects the body attachable unit (110), the communication terminal (120) is temporarily communicationally connected with the selected body attachable unit (110) (S205). And, the body attachable unit (110) transmits information of the body attachable unit (110) including PIN code information to the communication terminal (120) (S207). In this step, the body attachable unit (110) may transmit not only the PIN code information but also identifier information, serial number information of the body attachable unit (110), activation time information of the body attachable unit (110) and use period information of the body attachable unit (110) to the communication terminal (120).

The communication terminal (120) compares whether the PIN code information received from the body attachable unit (110) and the PIN code information acquired by recognizing the image recognition code are identical to each other (S209), and if the PIN code information received from the body attachable unit (110) and the PIN code information acquired by recognizing the image recognition code match each other, the communication terminal (120) completes the communication connection with the selected body attachable unit (110) (S211). However, if the PIN code information received from the body attachable unit (110) and the PIN code information acquired by recognizing the image recognition code are different from each other, the communication terminal (120) does not proceed the communication connection with the selected body attachable unit (110) any more and terminates the communication.

As described above, if the near field communication of the body attachable unit (110) and communication terminal (120) is connected, the communication terminal (120) transmits user information and the connection information acquired through the image recognition code to the server (150) (S213). In this step, the information transmitted by the communication terminal (120) to the server (150) may comprise information of a user which is logged in to the communication terminal (120), or any other information acquired through the image recognition code. Accordingly, if information of a serial number of the body attachable unit (110), a model name, a use time period and the PIN code is included to the image recognition code, all listed information can be the information transmitted to the server (150).

The server (150) stores the information transmitted from the communication terminal (120), and can store that information in association with information of the user received from the communication terminal (120) which transmits that information. Accordingly, the server (150) can store the information of the user connected to the communication terminal (120) and information acquired by recognizing the image recognition code associated with each other. Therefore, information regarding who uses a communication terminal (120) and which body attachable unit (110) is used can be stored to the server (150).

Here, the information of the user who uses the communication terminal (120) may be a user ID and so on, and, if necessary, may be a type of the communication terminal (120) and a network address (IP address or MAC address, etc.) of the communication terminal (120).

As described above, the operation that the information of the user as well as information included in the image recognition code are stored to the server (150) is for using the information stored in the server (150) when the near field communication connection of the communication terminal (120) and the body attachable unit (110) is reconnected after their disconnection. As previously described, the image recognition code can be printed directly on the body attachable unit (110), but, in a certain case, can be printed at the applicator (130) for attaching the body attachable unit (110) to the skin of the human body, or a package wrapping the body attachable unit (110).

Therefore, when the near field connection is disconnected while the user is using the body attachable unit (110) and the communication terminal (120) (S215), the near field communication of the body attachable unit (110) and the communication terminal (120) needs to be reconnected, but if the image recognition code is not directly printed on the body attachable unit (110), it may happen that the identifier information or the PIN code information of the body attachable unit (110) and so on cannot be found due to disposal or lost of the applicator (130), the protection cap (140) or the package.

At step S213, the communication terminal (120) transmits necessary information to the server (150) for backup, and therefore, as described above, when the body attachable unit (110) is reconnected to the communication terminal (120), the information stored in the server (150) can be used.

In this case, the communication terminal (120) requests the server (150) to transmit information of the body attachable unit (110) for reconnecting the near field communication connection with the body attachable unit (110) of which communication connection with the communication terminal (120) is disconnected (S217). In this step, the server (150) can perform verification regarding a user of the communication terminal (120) which requests the information, and the verification of the user can be performed based on whether the ID of the user who is logged in to the communication terminal (120) and the ID of the user registered to the server match each other. Additionally, a serial number of the communication terminal (120) or network information of the communication terminal (120) can be used.

Here, the communication of the server (150) and the communication terminal (120) can be implemented by communication through internet network, near field communication network, mobile communication or wifi communication. And, the communication with the server (150) can be performed by the communication unit (121) comprised in the communication terminal (120).

If the verification regarding the user is completed by the server (150), the list of the body attachable units (110) which the user has used is transmitted to the communication terminal (120) (S215). In this step, the information about all body attachable units (110) which the user has used can be transmitted to the server (150). However, the present disclosure is not limited thereto, and information of one or more body attachable units (110) in which the use period has not expired among all body attachable units (110) which the user has used can be transmitted from the server (150) to the communication terminal (120).

At step S207, when the body attachable unit (110) transmits the code information to the communication terminal (120), activation time information of the body attachable unit (110) and use period information (or expiration information) of the body attachable unit (110) can also be transmitted, and therefore at step 213, when the communication terminal (120) transmits the information to the server (150), activation time information of the body attachable unit (110) and use period information (or expiration information) of the body attachable unit (110) can also be transmitted. Accordingly, the server (150) can check information on the body attachable unit (110) of which user period has not been expired using the activation time information and the information of the use period of the body attachable unit (110) transmitted at step S213. Therefore, the server (150) can transmit only the list of one or more body attachable units (110) of which use period has not expired at the time when the communication terminal (120) requests the information about the body attachable unit (110) to the server (150).

If the communication terminal (120) receives the list of the body attachable units (110) from the server (150), the selection of one body attachable unit (110) from the list of the body attachable units (110) received from the communication terminal (120) is performed (S221). Accordingly, the list of the body attachable units (110) received from the server (150) is listed and displayed on the display of the output unit (125) of the communication terminal (120), and the user can select one among the body attachable units (110) displayed on the communication terminal (120).

At step S219, a case that the list of the body attachable units (110) transmitted from the server (150) to the communication terminal (120) is not transmitted may happen. This case may happen because the server (150) has no attachable body unit (110) with unexpired use period in the information on the body attachable units (110) which have been used by the user. Therefore, because the server (150) has no list of the body attachable units (110) to be transmitted to the communication terminal (120), the transmission may not be performed. In this case, at step S221, the list of the body attachable units that can be selected is not displayed, and a guide or message indicating that there is no body attachable unit (110) that can be selected can be outputted on the communication terminal (120). When a guide or message indicating that there is no body attachable unit (110) that can be selected is displayed on the communication terminal (120), the communication terminal (120) terminates the communication connection with the body attachable unit (110).

At step S221, when the selection of the body attachable unit (110) is completed, the communication terminal (120) requests the information related to the body attachable unit (110) to the server (150).

The server (150) transmits to the communication terminal (120) the information related to the body attachable unit (110) in response to the request for the information related to the body attachable unit (110) from the communication terminal (120) (S225). In this step, the information related to the body attachable unit (110) which the server transmits to the communication terminal (120) is PIN code information of the body attachable unit (110) only, but the present disclosure is not limited thereto, and if necessary, whole or partial information related to the body attachable unit (110) which is stored in the server (150) can be transmitted.

If the communication terminal (120) receives the PIN code of the body attachable unit (110) from the server (150), the near field communication connection with the body attachable unit (110) is performed using the received PIN code (S227).

As described above, the foregoing detailed descriptions regarding the present disclosure have been presented by way of exemplary embodiments, but the detailed exemplary embodiments are presented as preferred examples, and therefore it should be understood that the present disclosure shall not be limited to those exemplary embodiments, and the scope of the present disclosure shall be defined by the Claims and all of their equivalents fall within the scope of the present disclosure.

What is claimed is:

1. A near field communication connection method comprising:

acquiring connection information of a body attachable unit, which is attachable to a human body to continuously monitor blood glucose, to connect communication between the body attachable unit and a communication terminal, wherein the body attachable unit stops monitoring the blood glucose after a use period of the body attachable unit has expired and is one time disposable such that the body attachable unit is disposed after one time use;

using an identifier of the body attachable unit included in the connection information, searching for and select the body attachable unit corresponding to the identifier of the body attachable unit among one or more devices which are connectable to communicate with the communication terminal;

connecting the communication between the selected body attachable unit and the communication terminal using an identification number of the body attachable unit included in the connection information, wherein the near field communication connection method further comprises:

transmitting, by the communication terminal and to a server, an activation time information and the use period information of the body attachable unit; and when the connection information of the body attachable unit is requested to the server to reconnect the communication between the body attachable unit and the communication terminal after the connected communication between the body attachable unit and the communication terminal has been disconnected:

checking, by the server and using at least the activation time information and the use period information of the body attachable unit and the activation time information and the use period information of other body attachable units received by the server, for a first set of body attachable units for which use periods have not been expired among one or more body attachable units which that have been communicationally connected to the communication terminal, the body attachable unit being one of the one or more body attachable units that have been communicationally connected to the communication terminal;

transmitting, by the server, to the communication terminal a list of the first set of body attachable units for which use periods have not been expired among the one or more body attachable units that have been communicationally connected to the communication terminal;

requesting, by the communication terminal, the connection information of the body attachable unit in the list to which the communication terminal tries to be communicationally connected;

transmitting, by the server, the connection information of the body attachable unit requested by the communication terminal; and reconnecting the communication between the communication terminal and the body attachable unit using the connection information of the body attachable unit received from the server.

2. The near field communication connection method of claim 1, wherein the communication terminal recognizes an image recognition code including information of the identifier and the identification number to acquire the connection information of the body attachable unit.

3. The near field communication connection method of claim 1, wherein the communication between the communication terminal and the body attachable unit is connected according to a Bluetooth communication standard.

4. The near field communication connection method of claim 2, wherein the image recognition code is a QR code or a bar code.

5. The near field communication connection method of claim 1, further comprising, when the body attachable unit is selected, receiving, by the communication terminal, the identification number of the selected body attachable unit from the selected body attachable unit, wherein the connecting of the communication between the selected body attachable unit and the communication terminal comprises, if the identification number of the selected body attachable unit received from the selected body attachable unit is identical to the identification number of the body attachable unit included in the connection information, connecting the communication between the selected body attachable unit and the communication terminal.

6. The near field communication connection method of claim 1, further comprising, after the communication between the body attachable unit and the communication terminal is connected, transmitting information of a user of the communication terminal and the connection information of the body attachable unit to the server.

7. The near field communication connection method of claim 6, wherein the information of the user comprises one or more of an ID of the user logged into the communication terminal, a serial number of the communication terminal, and a network address of the communication terminal.

* * * * *